United States Patent [19]
Hsu

[11] Patent Number: 5,504,055
[45] Date of Patent: Apr. 2, 1996

[54] METAL AMINO ACID CHELATE

[75] Inventor: Hsinhung J. Hsu, Ventura, Calif.

[73] Assignee: J.H. Biotech, Inc., Ventura, Calif.

[21] Appl. No.: 213,263

[22] Filed: Mar. 15, 1994

[51] Int. Cl.$^6$ .......................... A01N 33/08; A01N 37/00; A01N 37/44

[52] U.S. Cl. .................. 504/121; 504/191; 71/27; 71/DIG. 2; 514/492; 514/494; 514/499; 514/501; 514/502; 514/561; 514/574

[58] Field of Search ...................................... 504/121, 191; 71/27, DIG. 2; 514/492, 494, 499, 501, 502, 561, 574

[56] References Cited

U.S. PATENT DOCUMENTS

| | | | |
|---|---|---|---|
| 3,962,416 | 6/1976 | Katzen | 424/19 |
| 4,436,547 | 3/1984 | Sampson | 71/76 |
| 4,830,716 | 5/1989 | Ashmead | 204/72 |
| 5,298,482 | 3/1994 | Tanaka et al. | 504/320 |

*Primary Examiner*—S. Mark Clardy

[57] ABSTRACT

A water soluble metal amino acid chelate is prepared by adding a metal salt to deaerated water, mixing the salt solution with a mixture of an amino acid and an organic acid and adjusting the pH of the resulting composition to a range of from about 4.5 to about 8.5 to produce a clear solution. The resultant clear solution can then be applied to plants or it can be dried for storage. The water soluble metal amino acid chelate produced by the process, when applied to plants, results in increased metals assimilation and improved plant growth.

13 Claims, 1 Drawing Sheet

METAL AMINO ACID CHELATE

BACKGROUND

This invention relates to a method of preparing stable amino acid chelates. Moreover, this invention relates to a stable new form of amino acid chelates and to the new chelate prepared by the process.

Certain metal ions are known to be beneficial in stimulating plant growth and in the production of larger, stronger plants, increased production of fruits or vegetables or the generation of more flavorful produce. Other benefits have been observed when these metals are added to the diet of animals and humans.

It has become generally accepted that the chelated forms of these metals with amino acids are demonstrably better assimilated by plants, animals, and human beings than metal salts, the plant, animal and human tissues showing increased metal content when exposed to metal amino acid chelates. Prior art metal amino acid chelates are formed by reacting metal salts with amino acids. For example, metal salts, such as salts of iron, zinc, copper, magnesium, cobalt or calcium, when reacted with an amino acid, for example glycine, would form ferrous glycinate, zinc glycinate, copper glycinate, magnesium glycinate, cobalt glycinate, cobalt glycinate, or calcium glycinate. However, the metal amino acid chelates made according to the prior art processes result in products that are insoluble or unstable in water, particularly at a low pH or a pH above 7. The chelation process shown in certain prior art references requires heating under nitrogen (U.S. Pat. Nos. 2,877,253 and 2,957,806). Other prior art techniques produce chelates which are unstable or precipitate at a pH above 8 (U.S. Pat. Nos. 4,216,143 and 4,216,144). Additionally, these prior art chelates have been known to precipitate out of solution when other chemical compounds, such as phosphates, are added to the chelate solution.

Prior art chelates also show stability problems over a period of time, the compounds precipitating after two or three days (U.S. Pat. No. 4,216,144). U.S. Pat. No. 3,396,104 shows formation of insoluble metal proteinates using saline water.

Therefore, there is a real need for a material capable of delivering high levels of desirable metal ions to plants, animals or human beings. The utility of such a material would be further enhanced if it is soluble in both acid, neutral and basic aqueous solutions, particularly if the materials remain in solution even after the addition of other soluble materials.

SUMMARY

These needs are met by the process for preparing metal amino acid chelates of the present invention.

The present invention is directed to a process for preparing metal amino acid chelates, and the metal amino acid chelates prepared by the process. Further, the present invention is directed to metal amino acid chelates which are soluble in water where the solution has a pH from about 4.5 to about 8.5. Still further the invention is directed to metal amino acid chelates which are stable over an extended period of time, the stability or solubility not being adversely effected by the addition of other additives to the solution.

The process for preparing metal amino acid chelates of the present invention comprises the production of a solution of the desired metal ion by dissolving a water soluble salt of the metal in deaerated water, adding the salt solution to an acid solution prepared by mixing an organic acid with an amino acid to form a chelate, and adjusting the pH of the solution to a pH between 4.5 and 8.5.

The process results in a chelate of the metal ion with the amino acid and the organic acid, the chelate having a unique composition as demonstrated by the spectral analysis.

BRIEF DESCRIPTION OF DRAWINGS

These and other features, aspects, and advantages of the present invention will become better understood with reference to the following description, appended claims, and accompanying drawing, where:

DESCRIPTION

Figure 1:
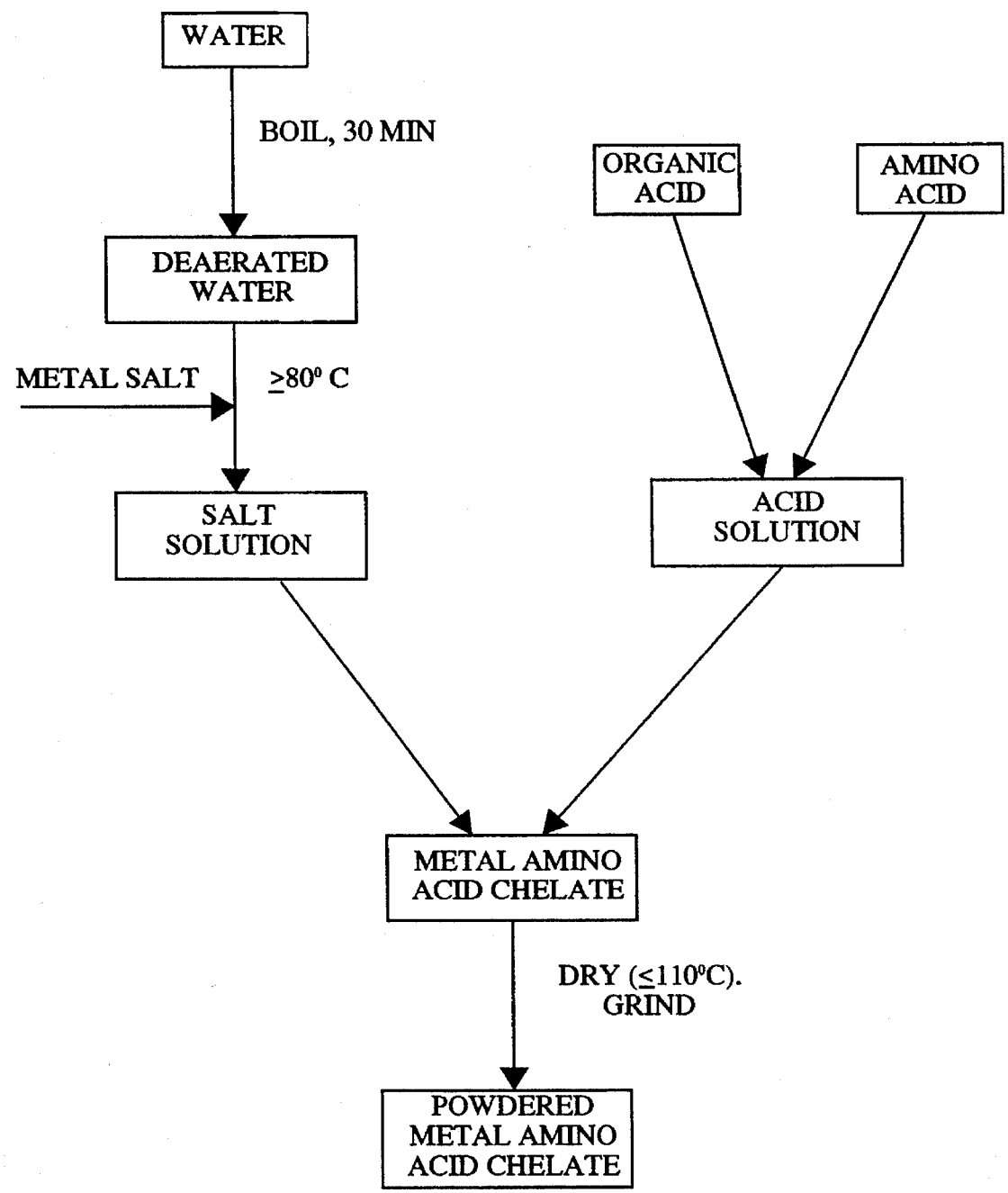
FIG. 1 is a flow diagram depicting an exemplary chelate formation process having features of the invention.

FIG. 1 depicts an exemplary process embodying features of the invention. Water is deaerated by boiling for at least 30 minutes. A quantity of a water soluble salt of the desired metal ion is then added to the deaerated water with stirring, the solution being maintained at a temperature of at least about 80° C. An acid solution is also prepared by mixing an organic acid with an amino acid, the two acids being combined in a ratio of about 1:1 to about 1:10, the ratio of the two acids being dependent on the number of —NH2, or —COOH groups in each compounds and/or the valence of the metal ion to be added. While not required, it is preferred that each solution is filtered prior to proceeding with the next step so that the mixtures do not include any undissolved material.

The metal salt solution and the acid solution are then combined with mixing so that the mole ratio of metal ion to acid is about 1:2, the mixture being maintained at 80° C. to produce a metal amino acid chelate solution. Undissolved material can then be filtered from the chelate solution and the chelate solution can be applied to a plant or soil in which the plant is growing. Alternatively, the chelate solution can be dried by standard processing techniques, the dried material converted to fine granules or powder and the resultant dry material packaged for later use. If the product is not used in its liquid state but instead is dried, the maximum drying temperature was about 110° C. Higher temperatures tended to cause decomposition of the chelate.

The process of the invention is applicable to a broad range of metal ions including water soluble salts of iron, cobalt, copper, zinc, manganese, magnesium, calcium, boron, molybdenum, and nickel or mixtures thereof. A list of representative metal salts includes the water soluble carbonates, sulfates, nitrates, oxides, hydroxides, chlorides, phosphates and acetates or mixtures thereof.

A broad range of organic acids, including acids with more than one carboxyl groups and one or more hydroxyl groups, and amino acids have also been found to be usable in the process of the invention. Suitable organic acids include citric acid, malonic acid, tartaric acid, lactic acid and gluconic acid or mixtures thereof. Amino acids, with or without the addition of a broad range of substituents including, but not limited to a second carboxyl group (i.e., aspartic acid or glutamic acid), a carboxamide (i.e., asparagine), a second basic group such as an amino group (i.e., lysine), an guanidino group (i.e., arginine), an imidazole ring (i.e., histidine), a benzene or heterocyclic ring system, phenolic or alcoholic hydroxyl groups, halogen or sulfur atoms are suitable for the process of the invention. Preferred amino acids include glycine, lysine, methionine, cysteine, glutamic acid and aspartic acid and mixtures thereof. Increasing the pH up to about 8.5 does not affect the clear character of the solution.

The preferred base for adjusting the pH is potassium hydroxide which also resulted in a chelate with the potassium present. Sodium hydroxide is also suitable. Alternatively, uses of ammonium hydroxide results in a chelate with an increased nitrogen content. Thus, in addition to producing a chelate with an enhanced ability to deliver a metal ion to a treated plant, the use of these materials also allows the delivery of potassium, and/or nitrogen to the plant. These materials are also recognized as being beneficial to the production of healthy plants and better produce.

Highly critical to the invention is the deaeration of the water used to produce the chelate. The presence of dissolved oxygen appears detrimental to the end product as it can result in a shifting of the valence state of the metal (e.g., $Fe+2$ to $Fe+3$).

It is also important that the calcium and magnesium content of the water be reduced or eliminated. Suitable procedures include distillation, deionization or softening the water.

The metal amino acid chelate solution prepared according to the process of the invention had a mineral content in the range of 250 to 50,000 parts per million.

The chemical structure of the metal amino acid chelate is believed to be:

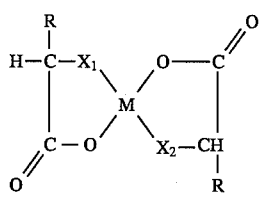

Where $X_1=NH_2$ and $X_2=NH_2$ or 0 M is a metal ion and R a carbon containing a compound derived from the amino acid or organic acid with or without the addition of —S, —$NH_3$, —COOH or other groups commonly making up amino acids or organic acids. There are two molecules of the chelating agent to 1 molecule of metal. A ring structure is formed between each of the chelating agents and the metal.

It is possible that organic acid may substitute for some of the amino acid groups. In this case, one of the chelating agent is amino acid and the other one is organic acid and at least one —X in the formula is —O and R represents constituents of common organic acids. This may increase the stability of the chelates.

In order to more clearly define the invention, the following examples of methods of preparation are set forth. These examples are illustrative only and are not limiting as to the scope of the invention. Examples I, II, V, VI, IX, X, XI, XII, and XIII set forth processes embodying features of the invention. Examples III, IV, VII and VIII are representative of prior art. The seven experiments which follow the Examples demonstrate the superiority of the chelate prepared according to the process of the invention over the prior art products claimed herein.

EXAMPLE I (iron/citrate/glycine chelate)

(1) 1,000 grams of water were placed in a beaker, heated to 100° C. followed by boiling for 30 minutes.

(2) 133 grams of ferrous carbonate monohydrate were added to the boiling water and the mixture was stirred constantly while keeping the temperature of the mixture at or above about 80° C.

(3) 30 grams of citric acid were mixed with 150 grams of glycine and then the acid mixture was add to the ferrous carbonate solution.

(4) The temperature of the mixture was maintained at or above about 80° C. with constant stirring until the no more solid went into solution.

(5) The mixture was filtered to remove the undissolved materials and the filtrate was dried at a temperature not in excess of 110° C.

(6) The dry material, referred to as an iron amino acid chelate, was labeled as Sample I.

EXAMPLE II (iron/citrate/glycine chelate)

(1) 1,000 grams of water were boiled for 30 minutes to remove dissolved air.

(2) 170 grams of ferrous sulfate monohydrate were dissolved in the deaerated water and the solution was maintained at 80° C.

(3) 30 grams of citric acid were mixed with 150 grams of glycine and the acid solution was added to the ferrous sulfate solution with stirring. The temperature of the mixture was maintained at about 80° C. until no more solids would dissolve.

(4) The mixture was filtered to remove any undissolved materials, the filtrate was dried at about less then about 110° and the dry material was ground to a fine powder.

(5) The ground material, referred to as an iron amino acid chelate, was labeled as Sample II.

EXAMPLE III (Prior Art)

(1) 1,000 grams of water were brought to a boil and allowed heat to boil for 30 minutes to remove air.

(2) 133 grams of ferrous carbonate monohydrate were added to the boiling water. The mixture was stirred constantly and the temperature of the mixture was maintained at about 80° C.

(3) 150 grams of glycine were added to the ferrous carbonate solution.

(4) The temperature of the mixture was held at about 80° C. with continuous mixing until no more material would dissolve.

(5) The mixture was filtered to remove the undissolved materials, the filtrate was dried at 110° C., and the dry material was ground to produce a powder. The material was labeled as Sample III.

EXAMPLE IV (Prior Art)

(1) 1,000 grams of water were boiled for 30 minutes to remove dissolved air.

(2) 170 grams of ferrous sulfate monohydrate were added to the deaerated water.

(3) 150 grams of glycine were added to the ferrous sulfate solution.

(4) The temperature of the mixture was maintained at about 80° C. with continuous mixing until no more material would dissolve.

(5) The mixture was filtered to remove any undissolved materials, the filtrate was dried at 110° C., and the dry material was ground to a powder.

(6) The grind material was labeled as Sample IV.

EXAMPLE V (calcium/malonic/lysine chelate)

(1) 1,000 grams of water were boiled for 30 minutes to remove dissolved air.

(2) After the water cooled, 100.1 grams of calcium carbonate were added to the deaerated water with constant stirring.

(3) 60 grams of malonic acid were mixed with 292.5 grams of lysine and then the acid mixture was added to the calcium carbonate solution.

(4) The mixture was stirred until no more material would dissolve, the mixture was filtered to remove the undissolved materials, and the filtrate was dried at less then about 110° C.

(5) The dry material was ground and labeled as Sample V.

EXAMPLE VI (calcium/malonic/lysine chelate)

(1) 1,000 grams of water were boiled for 30 minutes to remove dissolved air.

(2) After the water cooled, 111.0 grams of calcium chloride were added to the deaerated water with constant stirring.

(3) 60 grams of malonic acid were mixed with 292.5 grams of lysine and the acid solution was added to the calcium chloride solution.

(4) The mixture was stirred continuously until no more material would dissolve, the mixture was filtered to remove the undissolved materials, and the filtrate was dried at 110° C.

(5) The dry material was ground to a powder and labeled Sample VI.

EXAMPLE VII (Prior Art)

(1) 1,000 grams of water were boiled for 30 minutes to remove dissolved air.

(2) After the water cooled, 100.1 grams of calcium carbonate were added to the deaerated water with constant stirring.

(3) 292.5 grams of lysine were added to the calcium carbonate solution.

(4) The mixture was stirred continuously until no more material would dissolve, the mixture was filtered to remove any undissolved materials, and the filtrate was dried at 110° C.

(5) The dry material was ground to a powder and labeled as Sample VII.

EXAMPLE VIII (Prior Art)

(1) 1,000 grams of water were boiled for 30 minutes to remove any dissolved air.

(2) 111.0 grams of calcium chloride were added to the deaerated water with constant stirring.

(3) 292.5 grams of lysine were added to the calcium carbonate solution.

(4) The mixture was stirred continuously until no more material would dissolve, the mixture was filtered to remove any undissolved materials, and the filtrate was dried at 110° C.

(5) The dry material was ground to a powder and labeled as Sample VIII.

EXAMPLE IX (copper/citrate/aspartic chelate)

1. 1,000 grams of water were boiled for 30 minutes to remove air.

2. After the water cooled, 97.6 grams of cupric hydroxide were added to the deaerated water with constant stirring.

3. 30 grams of citric acid were mixed with 266.2 grams of aspartic acid and then the acid solution was added to the cupric hydroxide-water mixture.

4. The mixture was held at about 80° C. and with constant stirring until no more material would dissolve and the mixture was passed through a filter to remove any undissolved materials.

5. The filtrate was dried at less then about 110° C. to obtain a copper amino acid chelate.

EXAMPLE X (magnesium/citrate/glycine chelate)

1. 1,000 grams of water were boiled for 30 minutes to remove air.

2. After the water cooled, 24.3 grams of powdered magnesium metal were added to the deaerated water with constant stirring.

3. 30 grams of citric acid were mixed with 150 grams of glycine and the acid solution was added to the magnesium-water mixture.

4. The mixture was held at about 80° C. with continuous stirring until no more material would dissolve and the mixture was passed through a filter to remove the undissolved materials.

5. The filtrate was dried at less than about 110° C. to obtain a magnesium amino acid chelate.

EXAMPLE XI (zinc/citrate/glutamate chelate)

1. 1,000 grams of water were boiled for 30 minutes to remove air.

2. After the water cooled, 81.4 grams of zinc oxide were added to the deaerated water with constant stirring.

3. 30 grams of citric acid were mixed with 294.2 grams of glutamic acid and then added to the zinc oxide-water mixture.

4. The mixture was held at about 80° C. with continuous stirring until no more material would dissolve and the mixture was passed through a filter to remove the undissolved materials.

5. The filtrate was dried at less than about 110° C. to obtain a zinc amino acid chelate.

EXAMPLE XII (manganese/citrate/methionine chelate)

1. 1,000 grams of water were boiled for 30 minutes to remove air.

2. After the water cooled, 277.1 grams of manganous sulfate heptahydrate were added to the deaerated water with constant stirring.

3. 30 grams of citric acid were mixed with 298.5 grams of methionine and then added to the manganous sulfate heptahydrate-water mixture.

4. The mixture was held at about 80° C. with continuous stirring until no more material would dissolve and the mixture was passed through a filter to remove the undissolved materials.

5. The filtrate was dried at less than about 110° C. to obtain a manganese amino acid chelate.

EXAMPLE XIII (cobalt/citrate/cysteine chelate)

1. 1,000 grams of water were boiled for 30 minutes to remove air.

2. After the water cooled, 118.9 grams of cobalt carbonate were added to the deaerated water with constant stirring.

3. 30 grams of citric acid were mixed with 242.3 grams of cysteine and then the acid solution was added to the cobalt carbonate-water mixture.

4. The mixture was held at about 80° C. with continuous stirring until no more material would dissolve and the mixture was passed through a filter to remove the undissolved materials.

5. The filtrate was dried at less than about 110° C. to obtain a cobalt amino acid chelate.

Chemical Analysis

Chemical analysis using atomic absorption spectrophotometer indicates the following metal contents of the chelates and prior art compounds:

| Sample I (iron chelate) | 17.2% Fe |
| Sample II (iron chelate) | 15.1% Fe |
| Sample III (prior art) | 19.5% Fe |
| Sample IV (prior art) | 17.3% Fe |
| Sample V (calcium chelate) | 8.6% Ca |
| Sample VI (calcium chelate) | 8.3% Ca |
| Sample VII (prior art) | 9.9% Ca |
| Sample VIII (prior art) | 13.0% Ca |
| Sample IX (copper chelate) | 15.8% Cu |
| Sample X (magnesium chelate) | 11.2% Mg |
| Sample XI (zinc chelate) | 16.0% Zn |
| Sample XII (manganese chelate) | 9.0% Mn |
| Sample XIII (cobalt chelate) | 14.8% Co |

Using the materials prepared in Examples I–XIII, the following experiments were prepared.

EXPERIMENTS

Experiment 1

A solution was prepared by adding 50 grams of Sample I to 450 grams of distilled water. The process was repeated with 50 grams of each of Samples II, III, and IV. One ml of each of the four solutions was added to a solution containing 2 grams of dipotassium phosphate in 8 milliliter of water. The phosphate mixtures with the solutions prepared from Samples I and II did not precipitate upon initially mixing, after 24 hours or upon increasing the pH to 8.5. The mixtures of the phosphate with the solutions prepared from Samples III and IV, however, showed precipitate under all three conditions.

Experiment 2

Twenty tomato plants were grown under controlled condition in 700 grams of potting soil. After growing for 7 days the twenty plants were divided into five groups with four plants in each group. One group was retained as a control and was treated only with distilled water. Group two was sprayed with 15 ml of a solution of Sample I containing 250 ppm of iron. Groups three, four and five were likewise treated with solutions of Sample II, Sample III and Sample IV, respectively, each solution containing 250 ppm of iron. After being allowed to grow for an additional 5 days all of the plants were cut at the soil level, washed with 1% HCl, rinsed, and dried at 75° C. for 4 hours. Analysis revealed the following weights and average iron concentration:

| Solution | Plant Dry Weight | | Iron Conc. | |
| --- | --- | --- | --- | --- |
| | gms | % increase over control | ppm | % increase over control |
| Control | 5.30 | — | 131 | — |
| Sample I | 5.45 | 2.83 | 162 | 23.66 |
| Sample II | 5.68 | 7.17 | 170 | 29.77 |
| Sample III | 5.28 | −0.38 | 139 | 6.11 |
| Sample IV | 5.41 | 2.08 | 146 | 11.45 |

Experiment 3

A solution was prepared by adding 10.0 grams of Sample V to 100 ml of water. Similar solutions were prepared from 10 grams of each of Samples VI, Sample VII and Sample VIII. An ammonium sulfate solution (10 grams of ammonium sulfate in 90 grams of distilled water) was then added to each of the aqueous solutions of Samples V, VI, VII, and VIII. The mixtures with Sample V or VI did not produce a precipitate. Under the same conditions, but both of the Sample VII and VIII solutions resulted in precipitates. Repeating the experiment with dipotassium phosphate (100 grams per 400 grams of water) in place of the ammonium sulfate gave the same results.

Experiment 4

Eighteen tomato plants were grown under controlled condition in 1,000 grams of potting soil. Fifty millimeters of Hoagland's Nutrient solution without iron was applied to each pot twice a week. After growing for 7 days, the eighteen plants were divided into three groups with six plants in each group. One group was retained as control and was sprayed with only distilled water once a week. Group two was sprayed with 15 ml of a solution containing 200 ppm iron prepared from Iron Amino Acid chelate once a week. Group three was sprayed with 15 ml of a solution containing 400 ppm iron prepared from Iron Amino Acid chelate once a week.

After being allowed to grow for 45 days, all of the plants were cut at the soil level, washed with 1% HCL, rinsed with distilled water, and dried at 75° C. for 24 hours. The average dry weight of plant and iron concentration for each group are listed below:

| Treatment | Plant Appearance | Dry Weight | | Iron Conc. | |
| --- | --- | --- | --- | --- | --- |
| | | gms | % increase over control | ppm | % increase over control |
| Control | Yellow | 9.2 | — | 41 | — |
| 200 ppm Fe | Normal | 14.9 | 62.0 | 165 | 302 |
| 400 ppm Fe | Normal | 15.7 | 70.7 | 181 | 341 |

Experiment 5

Eighteen pots were prepared with 1,000 grams of potting soil in each pot. Eight corn seeds were planted in each pot. After the seedlings emerged, they were thinned to five plants per pot. The eighteen pots were then divided into three groups with six pots in each group. Hoagland's Nutrient solution without zinc was applied to each pot twice a week. When plants were about 4–6 inches tall, the materials listed were sprayed on plants as designated below once a week:

Group I - Distilled Water

Group II - 150 ppm Zn prepared from Zinc Amino Acid chelate (Example XI)

Group III - 300 ppm Zn prepared from Zinc Amino Acid chelate (Example XI)

Fifty days after planting, corn plants were cut at the soil level, washed with 1% HCL, rinsed with distilled water, and dried at 75° C. for 24 hours. After drying, plants were weighed and analyzed for zinc. The average dried weight and zinc concentration of corn plants from each group are listed below:

| Treatment | Dry Weight | | Zinc Conc. | |
|---|---|---|---|---|
| | gms | % increase over control | ppm | % increase over control |
| Group I | 2.69 | — | 34 | — |
| Group II | 3.28 | 21.93 | 48 | 41.18 |
| Group III | 3.45 | 29.0 | 61 | 82.35 |

Experiment 6

Eighteen pots were prepared with 1,000 grams of potting soil in each pot. Ten bean seeds were planted in each pot. After the seedlings emerged, they were thinned to five plants per pot. The eighteen pots were then divided into three groups with six pots in each group. Hoagland's Nutrient solution without manganese was applied to each pot twice a week. When plants were about 4–6 inches tall, the materials listed were sprayed on plants as designated below once a week:

Group I - Distilled Water

Group II - 150 ppm Mn prepared from Manganese Amino Acid chelate (Example XII)

Group III - 300 ppm Mn prepared from Manganese Amino Acid chelate (Example XII)

Fifty days after planting, plants were cut at the soil level, washed with 1% HCL, rinsed with distilled water, and dried at 75° C. for 24 hours. After drying, plants were weighed and analyzed for manganese. The average dried weight and manganese concentration of bean plants from each group are listed below:

| Treatment | Dry Weight | | Manganese Conc. | |
|---|---|---|---|---|
| | gms | % increase over control | ppm | % increase over control |
| Group I | 2.01 | — | 41 | — |
| Group II | 2.36 | 17.4 | 63 | 53.66 |
| Group III | 2.42 | 20.4 | 87 | 112.2 |

Experiment 7

Sixteen pots each containing five pounds of silica sand were divided into five groups with four pots in each group and ten corn seeds were planted in each pot. After germination, seedlings were thinned to five plants in each group. In addition to water, each pot received 50 milli meters of Hoagland's Nutrient solution without iron twice a week. When the plants were about 4–6 inches in height, the pot was sprayed, as indicated below, with 20 mls of the materials identified below:

| Treatment No. | Pot No. | Treatment |
|---|---|---|
| Control | 1–4 | Distilled Water |
| Iron Sulfate | 5–8 | 250 ppm Fe from Iron Sulfate |
| Fe-EDTA | 9–12 | 250 ppm Fe from Fe-EDTA |
| Iron Chelate | 13–16 | 250 ppm Fe from Iron Amino Acid Chelate (Example I) |

The spray was applied twice a week and continued until two weeks before harvest. Plants were allowed to grow for 45 days. At the end of the test, plants were cut at the surface level, weighed (fresh weight), washed with distilled water, and then dried in an oven at 75° C. for 24 hours. The dried samples were weighed and recorded as dry matter yield. The average results of each treatment of the tests are shown below:

| Treatment No. of control | Fresh Weight/plant(g) | | Dry Matter Yield/plant | |
|---|---|---|---|---|
| | gms | % increase over control | gms | % increase over control |
| Control | 9.48 | — | 1.02 | — |
| Iron Sulfate | 23.50 | 147.0 | 2.47 | 142 |
| Fe-EDTA | 25.72 | 171.3 | 2.68 | 162.75 |
| Iron Chelate | 26.39 | 178.4 | 2.91 | 185.3 |

Experiments 1 through 3 show that the amino acid chelated iron prepared according to a process embodying the invention (Samples I and II) are more stable than those taught by the prior art. The product prepared by the method taught herein did not result in a precipitate after standing for 24 hours or at a pH of 8.5, thereby overcoming significant limitations of prior products.

The plant test demonstrated that the iron chelates prepared as taught by this invention are better assimilated by plants as shown by the higher concentration of iron in the plants and the increased weight of the plants when compared with either the control or the metal compound not prepared in accordance with the process of the invention.

Furthermore, amino acid chelated calcium prepared according to the invention disclosed herein forms no precipitate with additions of either sulfate or phosphate solutions at the normal application concentrations. Prior art preparations precipitate with both phosphate and sulfate solutions. Since commonly used agricultural fertilizers include sulphate and phosphate solutions, the invention eliminates the mixing problems when using phosphates of sulfates with chelated metal amino acids.

Experiments 4–7 show that the use of chelated metals prepared according to the invention, in all instances, show marked improvement in metal uptake and weight of growth over controls than the use of unchelated metal.

Further, experimentation has shown that the solubility and stability of the metal amino acid chelates produced by the process of the invention is unexpected. For example, a metal sulphate (e.g., cobalt sulphate) mixed with an amino acid results in a non-soluble compound which forms a milky aqueous solution (an emulsion). Adjustment of the pH of the aqueous solution does not convert the emulsion to a solution. Additionally, a metal salt reacted with an organic acid (e.g., ferrous sulfate plus citric acid) produces an insoluble material (i.e., ferrous citrate). But, mixing a metal sulphate with a solution composed of an amino acid and an organic acid (e.g., glycine plus citric acid) produces a material insoluble at low pH which can be converted to a clear solution by raising the pH above about 4.5.

Although the present invention has been described in considerable detail with reference to certain preferred versions and uses thereof, other versions and uses are possible. For example, the time and temperature of the various steps in the process can be varied. Additionally, the invention contemplates a broad range of organic acids, amino acids and metal salts as well as a range of ratios of the components. Further, even though the invention has been described for use in treating plants, it is also contemplated that the metal containing chelates of the invention may be used in various other applications where it is desired to deliver higher levels of the metal ion or to increase the assimilation of the metal ion. Other uses for the metal amino acid chelates of the invention include, but are not limited to, the delivery of metal ions to animals or humans or as a reactant in chemical processes where the delivery of metal ions is required.

The process described can be used to prepare a chemical composition which has the unique capacity of increasing the uptake of desirable metallic ions in plants. In addition, the chemical compositions produced appear to be new compositions not shown in the prior art. Therefore, the spirit and scope of the appended claims should not be limited to the description of the preferred versions contained herein.

I claim:

1. A composition of matter comprising a metal complex produced by blending a metal salt, an amino acid and an organic hydroxy acid in deaerated water, the composition of matter being substantially soluble at a pH from about 4.5 to about 8.5, said complex having the structure:

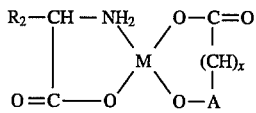

Where M = a metal ion,
x = 0 or 1,

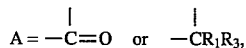

$R_1$ = the carbon chain from the organic hydroxy acid, which may be optionally substituted with —OH or —COOH.

$R_2$ = H, or the carbon chain radical from the α-position of the amino acid, and $R_3$ = —H or —COOH.

2. The composition of matter of claim 1 wherein the metal salt has an anion selected from the group consisting of sulfates, nitrates, chlorides, oxides, hydroxides, carbonates, phosphates, acetates, oxides and mixtures thereof and a cation selected from the group consisting of iron, cobalt, copper, zinc, magnesium, manganese, calcium, boron, molybdenum, nickel and mixtures thereof, the amino acid is selected from the group consisting of lysine, glycine, glutamic acid, aspartic acid, methionine, cysteine and mixtures thereof and the organic acid is selected from the group consisting of citric acid, lactic acid, malonic acid, tartaric acid, gluconic acid and mixtures thereof.

3. The composition of matter of claim 1 wherein the metal salt is selected from the group consisting of a water soluble salt of sulfate, carbonate, oxide, hydroxide and mixtures thereof.

4. The composition of matter of claim 1 wherein the organic acid is selected from the group consisting of citric acid, glutamic acid and malonic acid.

5. The composition of matter of claim 1 wherein the amino acid is selected from the group consisting of glycine, methionine, cysteine and lysine.

6. The composition of claim 1, wherein said composition is effective in increasing the growth rate and metal ion uptake of an agricultural product.

7. The substance of claim 6 wherein M is a metal ion selected from the group consisting of iron, cobalt, copper, zinc, magnesium, manganese, calcium, boron, molybdenum, nickel and mixtures thereof.

8. The substance of claim 6 wherein the amino acid is selected from the group consisting of glycine, methionine, lysine, cysteine, glutamic acid, aspartic acid and mixtures thereof.

9. The substance of claim 6 wherein the organic acid is selected from the group consisting of citric acid, malonic acid, tartaric acid, lactic acid, gluconic acid and mixtures thereof.

10. The composition of claim 6 wherein the metal ion is derived from a metal salt having an anion selected from the group consisting of sulfates, nitrates, chlorides, oxides, hydroxides, carbonates, phosphates, acetates, oxides and mixtures thereof and the metal ion is selected from the group consisting of iron, cobalt, copper, zinc, magnesium, manganese, calcium, boron, molybdenum, nickel and mixtures thereof and the organic acid is selected from the group consisting of citric acid, lactic acid, malonic acid, tartaric acid, gluconic acid and mixtures thereof.

11. The substance of claim 10 wherein the dry weight of tomato plants treated with the substance is at least 60% greater than the dry weight of control plants not treated with the substance.

12. The substance of claim 10 wherein the dry weight of corn plants treated with the substance is at least 26% greater than the dry weight of control plants not treated with the substance.

13. The substance of claim 10 wherein the dry weight of bean plants treated with the substance is at least 17% greater than the dry weight of control plants treated with the substance.

* * * * *